United States Patent
Mudryk et al.

(12) 
(10) Patent No.: US 6,365,742 B1
(45) Date of Patent: Apr. 2, 2002

(54) PREPARATION OF OPIATES, INTERMEDIATES AND USES OF SALTS

(75) Inventors: Bogdan Mudryk, East Windsor; Chester Sapino, Sewell, both of NJ (US); Jen-Sen Dung, Boothwyn, PA (US); Alice Sebastian, Deptford, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 09/571,378

(22) Filed: May 15, 2000

Related U.S. Application Data

(62) Division of application No. 09/107,509, filed on Jun. 30, 1998, now Pat. No. 6,090,943.

(30) Foreign Application Priority Data

Jun. 30, 1997 (GB) .............................. 9713703

(51) Int. Cl.⁷ ...................... C07D 471/08; C07D 471/04
(52) U.S. Cl. ........................................ 546/44; 546/45
(58) Field of Search ..................... 546/44, 45

(56) References Cited

U.S. PATENT DOCUMENTS

| | | | |
|---|---|---|---|
| 3,894,026 A | 7/1975 | Sohar et al. ................. | 546/44 |
| 4,045,440 A | 8/1977 | Rapoport et al. ............. | 546/44 |
| 4,472,253 A | 9/1984 | Schwartz ................. | 204/158 R |
| 4,795,813 A | 1/1989 | Schwartz ................... | 546/45 |
| 5,112,975 A | 5/1992 | Wallace ..................... | 546/45 |
| 5,366,979 A | * 11/1994 | Lawson ..................... | 514/282 |
| 6,090,943 A | * 7/2000 | Mudryk et al. ............... | 546/44 |

FOREIGN PATENT DOCUMENTS

| | | |
|---|---|---|
| DE | 902 257 | 1/1954 |
| GB | 1 260 699 | 1/1972 |

OTHER PUBLICATIONS

The Merck Index, Twelfth Edition, p. 1582, compound No. 9411, Published By Merck & Co., Inc. 1996.*
L.G. Wade Jr. Organic Chemistry, pp. 480, 499 and 500, Prentice Hall Inc. Publishers, 1987.*
Schwartz et al, J. Med. Chem., 24(12):1525–1528 (1981).
Noble, Synthesis, pp. 1–6, (1970) (XP002078241).
Seki, Chem. Pharm. Bull., 18(4):671–676 (1970) (XP002078242).
Ihara et al, Synlett, 6:436–436 (1993) (XP002078243).
"Houben Weyl: Methoden der Organischen Chemie, Bd. VI/Id" (1978) George T. Verlag, Stuttgart, p. 161 (XP002078244).

* cited by examiner

*Primary Examiner*—Alan L. Rotman
(74) *Attorney, Agent, or Firm*—Morgan, Lewis & Bockius LLP

(57) ABSTRACT

A process for the preparation of thebaine, its salts such as the bitartrate, and analogues thereof, together with a novel intermediate useful in said process are disclosed. Thebaine bitartrate is itself useful in the preparation of oxycodone; analogues are useful in the preparation of analogous 14-hydroxymorphinones.

12 Claims, No Drawings

PREPARATION OF OPIATES, INTERMEDIATES AND USES OF SALTS

This is a divisional of application Ser. No. 09/107,509, filed Jun. 30, 1998, now U.S. Pat. No. 6,090,943.

This invention relates to a process for the preparation of thebaine and analogues thereof, and to a novel intermediate useful in such a process. In particular, the invention relates to the preparation of thebaine from N-methyl morphinans, its isolation as a salt and the use of the salt in the preparation of N-methyl-14-hydroxymorphinones.

Thebaine is an N-methylmorphinan having the structure (A):

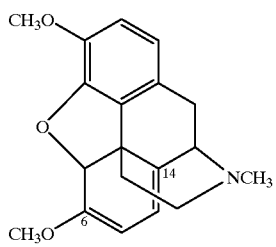

(A)

Thebaine and analogous compounds containing a dienol ether or a dienol ester are useful intermediates in the preparation of 14-hydroxymorphinans, such as oxycodone, naltrexone, nalbuphine and naloxone. Oxycodone is the corresponding 14-hydroxy-N-methylmorphinone (also called 14-hydroxy-7,8-dihydrocodeinone) having the structure (B):

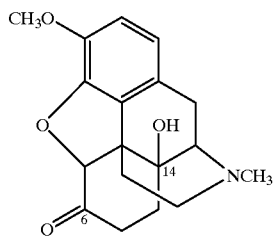

(B)

Unfortunately, thebaine is expensive and is not always readily available in industrially-required quantities. Sohar et al, U.S. Pat No. 3,894,026, disclose a method for producing thebaine, but the starting material is salutaridinol, which is itself not readily available. Therefore, it is desirable to prepare thebaine or its analogues, directly or through known intermediates, from more readily available morphinans such as codeine and morphine. Codeine is the corresponding 6-OH monoenolether analogue of thebaine.

Rapoport et al, U.S. Pat No. 4,045,440, provide a method for producing thebaine from codeine via the intermediate codeine methyl ether. This method requires a 90-second reaction time in preparation of the intermediate, and is thus not suitable for use on an industrial scale. The method also requires a 24-hour reaction period for conversion of the intermediate to thebaine, and employs a heterogeneous catalyst, manganese dioxide, for the transformation, leading to further difficulties on scale-up.

Schwartz, U.S. Pat Nos. 4,472,253 and 4,795,813 and J. Med. Chem. 24,1525 (1981) provides a method for producing certain dienol ester analogues of thebaine having the structural formula (C):

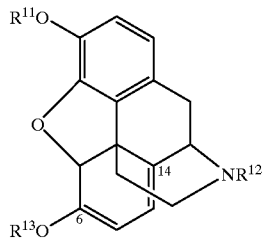

(C)

wherein $R^{11}$ is lower alkyl, $R^{12}$ is cyano or acyl, and $R^{13}$ is acyl. These thebaine analogues, in which the N-methyl group has been replaced by $R^{12}$, are useful as intermediates for naloxone, naltrexone and nalbuphine, but are not useful as intermediates to 14-hydroxy-morphinan compounds having an N-methyl group, such as oxycodone or oxymorphone. For these compounds, thebaine is the desired intermediate, since it has the required N-methyl substituent.

Further, the method of Schwartz, which employs a reaction temperature of 80–100° C. to introduce the $R^{12}$ acyl group, may not readily be extended to preparation of an N-methyl dienol ester, since at such a temperature, the N-methyl group would also be acylated, leading to by-products and reduced yield. Extension of this method to the preparation of N-methyl dienol ether compounds, such as thebaine, is also not feasible. At the reaction temperatures employed to introduce $R^{12}$, not only would the N-methyl group be alkylated, leading to by-products and reduced yield, but the alkylating agent would be destroyed by reaction with the base employed in the process.

Wallace, U.S. Pat No. 5,112,975, employs a process similar to that of Schwartz to prepare compounds of structural formula (C), but wherein the $R^{13}$ is an alkoxycarbonyl substituent. This process differs from that disclosed by Schwartz in that the ultimate starting material is morphine, rather than codeine, but has limited use as a method for preparing thebaine or thebaine analogues with N-alkyl substitution for the same reasons given in the preceding paragraph.

British patent number 1,260,699 discloses a method for preparation from codeine of dienol ethers analogous to thebaine. However, the method used for isolation of these dienol ethers is lengthy, requiring a chromatographic separation, and gives a low yield of the product. For these reasons, this method is not useful for large-scale preparation of thebaine.

It has now been found possible to provide an efficient, high-yielding process for the preparation of thebaine or thebaine analogues (i.e. having N-CH₃ substitution) containing a dienol ester or a dienol ether, from morphinone, codeinone or analogues thereof which contain an a,β-unsaturated ketone via a novel alkoxylated intermediate.

Accordingly, the present invention provides a process for the preparation of a compound of formula (I) or salt thereof:

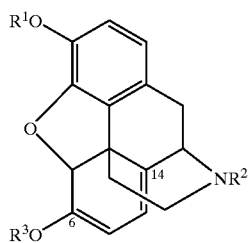

(I)

wherein $R^1$ and $R^3$ are the same or different and each is a protecting group; and
$R^2$ is lower alkyl, allyl or lower alkyl substituted by cycloalkyl; said process comprising the reaction of the compound of formula (III):

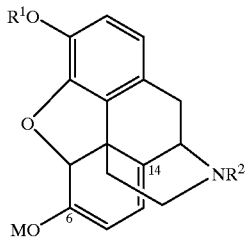

(III)

wherein $R^1$ and $R^2$ are as hereinbefore defined; and
M is an alkali metal or a quaternary ammonium cation;
with a compound of formula $R^3X$, wherein $R^3$ is as hereinbefore defined and X is a leaving group; and, optionally, but preferably,
the reaction of the compound of formula (I) so prepared with an acid, such as L-tartaric acid, to give a salt, such as the bitartrate, of the compound of formula (I).

Preferred protecting groups in the definition of $R^1$ and $R^3$ are selected from alkyl or acyl groups. Preferred alkyl groups are selected from lower alkyl, trialkylsilyl, alkyldiarylsilyl and acyl, although they may also be selected from aryl and alkylaryl, any of which alkyl and aryl groups may be substituted by halo. Preferred aryl groups are phenyl. Preferred acyl groups are selected from those of formula $R^4CO$—, wherein $R^4$ is selected from lower alkyl, lower alkyl substituted by halo or phenyl, and aryl, such as phenyl and substituted phenyl. $R^4$ is preferably selected from lower alkyl, phenyl or substituted phenyl. Preferably, alkyl groups herein have from 1–6, more preferably 1–4, carbon atoms; and aryl groups herein are phenyl, optionally substituted by alkyl and/or halo, such as chloro.

In an especially preferred aspect of the present invention, the compounds prepared by the above process are compounds of formula (I) wherein $R^1$, $R^2$ and $R^3$ may be the same or different and each is lower alkyl, for example $C_{1-6}$ alkyl, such as $C_{1-4}$ alkyl and preferably methyl or ethyl. In a particularly preferred aspect, the compound prepared is thebaine or a salt thereof, preferably the bitartrate salt.

Suitable agents $R^3X$ used in the preparation of the compounds of formula (I) include those alkylating or acylating agents where $R^3$ is preferred as defined hereinbefore. Suitable leaving groups X are halo, alkanoate, benzoate, substituted benzoate, alkyl sulphate, alkyl sulphonate, aryl sulphate, arylsulphonate, halosulphonate, haloalkylsulphonate, tetra-alkylammonium halide and dialkyl phosphate. Therefore, suitable alkylating agents $R^3X$ include dimethyl sulphate, diethyl sulphate, dibutyl sulphate, methyl methanesulphonate, methyl trifluoromethane sulphonate, alkylarylsulphonates, trialkylphosphates and trialkylsilyl chlorides. Preferably, the alkylating agent is dimethyl sulphate or diethyl sulphate.

Suitable acylating agents, $R^3X$, include acetic anhydride, propionic anhydride, acetyl chloride, propionyl chloride, and carboxylic acid anhydrides or halides derived from other alkyl or aryl carboxylic acids.

The alkylation/acylation is satiably carried out at a temperature of from –40° C. to +30° C. Although reaction at a higher temperature would produce the desired compound, alkylation or acylation of the tertiary nitrogen of the starting compound (a compound of formula (III)) or of the product (a compound of formula (I)) or of both may occur, leading to by-products and an accompanying yield loss, as previously mentioned.

The optional salt formation is carried out by dissolving the compound of formula (I) in a suitable solvent, which may be selected from those in which the salt to be formed is insoluble or from which it is capable of recrystallising, and thereafter treating the resulting solution with the corresponding acid, 1o such as tartaric acid, other organic acids, or inorganic acids such as hydrochloric acid, hydrobromic acid or perchloric acid, optionally at elevated temperature. Preferably, the bitartrate salt is formed by dissolving the compound of formula (I) in a suitable solvent, such as toluene or methanol, and treating the resulting solution with L-tartaric acid at a temperature of, for is example, 20–60° C. The bitartrate salt of the compound of formula (I) so formed may be further purified by crystallisation from, for example, aqueous methanol or ethanol.

The bitartrate salts of the compounds of formula (I) thereby prepared, particularly thebaine bitartrate, may then be used in the preparation of the corresponding 14-hydroxymorphinones, particularly oxycodone. It has surprisingly been found that the bitartrate salts, which generally include some water of hydration (e.g. thebaine bitartrate monohydrate), can be purified to the extent required for pharmaceutical grade 14-hydroxymorphinone analogues (e.g. oxycodone) to be prepared.

The conversion of the bitartrate salt to the 14-hydroxymorphinone analogue is preferably accomplished by a method analogous to that described herein in Example 8, comprising oxidation/dealkylation or deacylation followed by hydrogenation.

Accordingly, the present invention provides the use of a salt, preferably the bitartrate salt, of a compound of formula (I) as defined hereinbefore in the purification and/or preparation of a corresponding 14-hydroxymorphinone. Most preferred is the use of thebaine bitartrate in the preparation of oxycodone.

Compounds of formula (III) are novel and, accordingly, a still further aspect of the present invention provides a compound of formula (III) as hereinbefore defined. Preferred compounds of formula (III) are those wherein $R^1$, $R^2$ and M have the values described as preferred in the description above. Especially preferred is when $R^1$ and $R^2$ are both methyl, such as a derivative of thebaine or an analogue thereof, having a dienol ester or ether. Most preferred is when M is potassium, sodium or lithium, especially potassium.

Accordingly, the present invention further provides a process for the preparation of a compound of formula (III) as hereinbefore defined, which process comprises the reaction of a compound of formula (II):

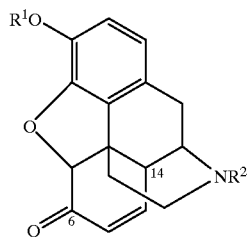

(II)

wherein R¹ and R² are as defined for formula (III), with an alkoxide base of formula MOR, wherein M is as defined for formula (III) and R is alkyl.

The reaction is suitably carried out in a solvent which will not react with the alkoxide base, but which readily dissolves both the base and the compound of formula (II), such as a dipolar aprotic solvent. Examples of such solvents are N-methylpyrrolidinone, N-methylcaprolactam, dimethyl sulphoxide, N,N-dimethylformamide, N,N-dimethylacetamide, tetrahydrofuran, 1,3-dimethyl-3,4,5,6-tetrahydro-2(IH)-pyrimidinone, and mixtures of these solvents with each other or with one or more aromatic hydrocarbon solvent(s), such as toluene. The preferred solvent is N-methylpyrrolidone.

The reaction is suitably carried out at a temperature ranging from −80° C to +60° C. Preferably, a dilute solution of the compound of formula (II) is added slowly to a solution of the base in order to minimise self-condensation. Preferred bases for this step include metal oxides, such as potassium tert-butoxide, potassium tert-pentoxide, sodium tert-butoxide or lithium tert-butoxide.

The invention will now be further described with reference to the following examples which are intended to illustrate but not limit the invention. The purity of the products of the examples was determined by reverse phase HPLC using the Waters Symmetry 4.6–100 mm C-18 3.5 μm column and the gradient method with water/acetonitrile as the mobile phase. The NMR spectra were run using a 300 MHz FT spectrometer.

REFERENCE EXAMPLE 1

CODEINONE

To a solution of codeine (100 g, 0.33 mol) in 1,2-dichloroethane (1000 mol) was added cyclohexanone (250 mol). From the above solution, 300 ml of 1,2-dichloroethane was distilled off in order azeotropically to remove any traces of water. The solution was then cooled to 50–60° C. Aluminium isopropoxide (17 g, 0.08 mol) was added to this solution in one portion, and the resulting solution was heated to reflux under an inert atmosphere for 1–2 hours. The reaction mixture was cooled to 5–10° C., extracted first with 0.9N HCl (570 mol) and then with water (100 mol). The combined aqueous extract was washed once with 1,2-dichloroethane (100 mol), treated with 3 g activated charcoal and then filtered through a pad of Celite.

Dichloromethane (500 mol) was added to the filtrate, and the biphasic mixture was cooled to 0–5° C. A 25% solution of NaOH (~60 mol) was added dropwise to this solution with vigorous stirring in order to bring the pH to 12. The organic layer was separated and the aqueous layer was extracted twice with 100 mol portions of dichloromethane. The combined organic layer was washed once with water (100 mol), dried over anhydrous sodium sulphate (50 g) and concentrated under reduced pressure. The crude product was recrystallised from ethyl acetate (1000 ml) to give codeinone (79.5 g, 80%). ¹H NMR (CDCl₃): 6.69–6.58 (m, 3H); 6.08 (dd, J=10.2, 2.7 Hz, 1H); 4.69 (s, 1H); 3.86 (s, 1H); 3.41 (dd, J=6, 3 Hz, 1H); 3.19 (dd, J=6, 3 Hz, 1H); 3.1 (d, J=18.3 Hz, 1H); 2.60 (ddd, J=12, 6, 3 Hz, 1H); 2.46 (s, 1H); 2.35–2.25 (m, 2H; 2.06 (dt, J=12, 6 Hz, 1H); 1.88–1.82 (m, 1H).

EXAMPLE 2

THEBAINE

A solution of codeinone, prepared according to reference example 1, (17.8 g) in N-methylpyrrolidinone (590 mol) was added over a period of 3 hours to a stirred solution of potassium tert-butoxide (10.4 g) in N-methyl-pyrrolidinone (145 mol) at 20° C. The contents of the flask (formation of dienolate salt confirmed in Example 7) were then cooled in an ice-water bath. Dimethyl sulphate (10.6 g) was added dropwise at a temperature of 3–7° C. The solution was stirred at 0–5° C. for 10 minutes and about 80 vol % of the solvent (600 mol) was distilled off under high vacuum (1–2 torr). The residual solution was diluted with toluene (200 mol) and poured into 5% aqueous solution of sodium chloride (500 mol). The organic layer was separated and the aqueous layer was extracted with toluene (2×100 ml). The combined organic layers were washed with water (2×180 ml) and dried with anhydrous sodium sulphate.

The solution of crude thebaine (~6 g) in toluene (200 ml) thus prepared was treated with formic acid (2 eq) and water (30 ml), and stirred for 10 minutes. The organic layer was extracted with 5% aqueous formic acid and the combined aqueous layers were then stirred with charcoal (0.6 g) for 20 minutes. After filtering through Celite, the filtrate was basified with ammonium hydroxide, stirred for 2 hours at 20° C. and 1 hour at 0° C. The solid was filtered, washed with cold water and dried to give 4.98 g (82% yield) of 94.0 area % pure thebaine. The latter was further purified by stirring its toluene solution (30 mol/g) with basic alumina (2 wt eq) for 1 hour at 20° C. The mass recovery of 98.7 area % pure thebaine was 95%. ¹H NMR (CDCl₃): 1.73 (dt, J=2.0 and 11.2 Hz, 1H); 2.20 (td, J=5.2 and 12.6 Hz, 1H); 2.46 (s, 3H); 2.60–2.70 (m,2H); 2.82 (td, J=3.6 and 12.6 Hz 1H); 3.32 (d, J=18.0 Hz, 1H); 3.60 (s) and 3.60 (m) (4H); 3.85 (s, 3H); 5.04 (d, J=6.4 Hz, 1 H); 5.29 (s, 1H); 5.55 (d, J=6.4 Hz, 1H); 6.59 (d, J=8.2 Hz, 1H); 6.66 (d, J=8.2 Hz, 1H).

EXAMPLE 3

THEBAINE BITARTRATE

After removal from the crude product of Example 2 of the drying agent by filtration, methanol (45 ml) was added and the toluene/methanol solution was treated dropwise with a solution of L-tartaric acid (9.9 g) in methanol (30 mol) at 40° C. The stirred suspension was allowed to cool to 0° C. and stirred at 0° C. for 1 hour. The solid was filtered off, washed with toluene and dried to give 27.5 g of crude thebaine bitartrate of 94 area % purity (HPLC) based on pure thebaine. The material was recrystallised from ethanol-water 3:1 (560 mol) to give 20.6 g (72% yield) of 99.8 area % (HPLC) pure thebaine bitartrate monohydrate. ¹H NMR (d₆-DMSO): 1.66 (d, J=13.0 Hz, 1H); 2.23 (td, J=5.6 and 13.0 Hz, 1H); 2.55 (s, 3H); 2.75–2.92 (m, 3H); 3.33 (d, J=18.6 Hz, 1H); 3.56 (s, 3H 3.75 (s, 3H); 3.96 (d, J=7.0 Hz, 1H); 4.13 (s, 2H); 5.17 (d, J=6.5 Hz, 1H); 5.33 (s, 1H); 5.69 (d, J=6.5 Hz, 1H); 6.63 (d, J=8.2 Hz, 1H); 6.74 (d, J8.2 Hz, 1H).

EXAMPLE 4

CODEINONE ETHYL DIENOL ETHER BITARTRATE

A solution of codeinone (17.8 g) in N-methylpyrrolidinone (590 mol) was added over a period of 3 hours to a stirred solution of potassium it tut-butoxide (10.4 g) in N-methylpyrrolidinone (145 ml) at 20° C. The contents of the flask (see Example 7) were then cooled In an Ice-water bath. Diethyl sulphate (12.9 g) was added dropwise at a temperature of 3–7° C. The solution was stirred at 0–5° C. for 10 minutes and worked-up as in Example 2. The crude bitartrate (23.6 g) was recrystallised from ethanol:water (3:1) (235 ml) to give 22.5 g(74% yield) of 98.9 area % pure (HPLC) codeinone ethyl dienol ether bitartrate hemitrihydrate. $^1$H NMR ($d^6$-DMSO): 1.27 (t, J=7.0 Hz, 3H); 1.65 (d, J=13.0 Hz, 1H); 2.23 (td, J=5.5 and 13.0 Hz, 1H); 2.56 (s, 3H); 2.75–2.94 (m, 3H); 3.75 (s, 3H) and 3.72–3.82 (m) (5H); 3.95 (d, J=7.0 Hz, 1H); 4.13 (s, 2H); 5.15 (d, J=6.5 Hz 1H); 5.32 (s, 1H); 5.68 (d, J 6.5 Hz, 1H); 6.74 (d, J=8.2 Hz, 1b); 6.74 (d, J=8.2 Hz, 1H). EXAMPLE 5

THEBAINE FROM CODEINONE AND METHYL TRIFLUOROMETHANESULPHONATE

Codeinone (300 mg) was added to a stirred suspension of potassium tert-butoxide (153 mg) in N,N-dimethylformamide (5 ml) at room temperature. After 10 minutes, methyl trifluoromethanesulphonate (164 mg) was added dropwise to the suspension. The solution was stirred for 5 minutes, diluted with ethyl acetate (30 ml), and then poured into water (50 ml). The aqueous phase was removed, and the organic phase was dried with sodium sulphate and evaporated, producing an orange solid. Analysis by HPLC against pure thebaine gave a thebaine content of 10%.

EXAMPLE 6

CODEINONE TERT-BUTYLDIMETHYLSILYL DIENOL ETHER

A solution of codeinone (250 mg) in tetrahydrofuran (10 ml) was cooled to 40° C. A 1.0M solution of sodium hexamethyldisilazide in tetrahydrofuran (1.18 ml) was added to the stirred solution. After 1 hour, a solution of tert-butyldimethylsilyl chloride (140 mg) in tetrahydrofuran (2 ml) was added dropwise. The reaction mixture was then allowed to warm to room temperature over a period of 1 hour. After stirring for 4 hours at room temperature, water (10 ml) was added, the mixture was made basic with ammonium hydroxide, and extracted with ethyl acetate (two 25 ml portions). The combined organic phases were extracted with water (two 15 ml portions), dried with sodium sulphate, and evaporated. Analysis by 300 MHz $^1$H NMR revealed that the solid contained 23% of the silylated dienolate product. The most diagnostic peaks of the silyl dienol ether were at 5.16 (s, H-5) and two doublets at 5.19 (J=6.3 Hz) and 5.46 (J=6.3 Hz) for the vinylic protons H-7 and H-8.

EXAMPLE 7

CODEINONE POTASSIUM DIENOLATE

A solution of codeinone (15 mg) in $d_9$-N-methylpyrrolidinone was added dropwise to a stirred solution of potassium tert-butoxide (10 mg) in $d_9$-N-methylpyrrolidinone (0.4 mol). A 300 MHz $^1$H NMR spectrum of the solution showed that complete deprotonation of the codeinone had occurred, as evidenced by the absence of the vinylic signals characteristic of codeinone {δ5.99 (dd, J=2.9, 10.2 Hz); 6.90 (dd, J=1.7, 10.2 Hz)}. Formation of the dienolate was confirmed by the presence of two signals corresponding to the dienolate structure {δ4.25 (d, J=6.5 Hz); 5.49 (d, J=6.5 Hz)}. The spectrum showed no evidence of significant dienolate decomposition when the solution was heated to 60° C.

EXAMPLE 8

USE OF THEBAINE BITARTRATE IN PREPARATION OF OXYCODONE

30% Hydrogen peroxide (7.1 g) was added to a solution of thebaine bitartrate monohydrate (20 g) (see Example 3) in isopropanol (40 ml), water (40 mol) and formic acid (60 ml) at 0–5° C. The solution was stirred for 30–40 minutes at 0–5° C. and for 2 hours at 45–50° C. The mixture was then transferred to a Parr shaker containing 5%Pd/BaSO$_4$ (1.6 g) and hydrogenated at 12–14 psi at 20° C. for 2 hours. The catalyst was removed by filtration through Celite, the filtrate was diluted with water (400 ml) and cooled to 0–5° C. After dropwise addition of 50% aqueous sodium hydroxide solution within 40 minutes at 0–20° C., the crude oxycodone base was filtered, washed with water and dried to give 12.0 g (91% yield) of oxycodone of 98.9 area % (HPLC) purity. is $^1$H NMR (CDC1$_3$): 1.53–1.68 (m, 2H); 1.87 (ddd, J=3.0, 5.0 and 13.3 Hz, 1H); 2.11–2.22 (m, 1H); 2.29 (dt, J=3.1 and 14.3 Hz, 1H); 2.35–2.49 (m, 2H); 2.40 (s, 3H); 2.56 (dd, J=5.9 and 18.6 Hz, 1H); 2.86 (d, J=5.9 Hz, 1H); 3.02 (td, J=5.1 and 14.4 Hz, 1H); 3.16 (d, J=18.6 Hz, 1H); 3.90 (s, 3H); 4.65 (s, 1H); 6.63 (d, J=8.2 Hz, 1H); 6.70 (d, J=8.2 Hz, 1H).

EXAMPLE 9

USE OF CODEINONE ETHYL DIENOL ETHER BITARTRATE IN PREPARATION OF OXYCODONE

The ethyl analogue of thebaine bitartrate (see Example 4) was successfully employed in the preparation of oxycodone using the same conditions as in Example 8.

What we claim is:

1. A process for the preparation of a compound of formula (I) or salt thereof:

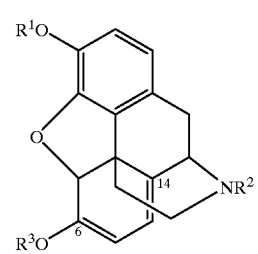

(I)

wherein $R^1$ and $R^3$ are the same or different and each is a protecting group; and $R^2$ is selected from the group consisting of lower alkyl, allyl and lower alkyl substituted by cycloalkyl;

said process comprising the reaction of the compound of formula (III):

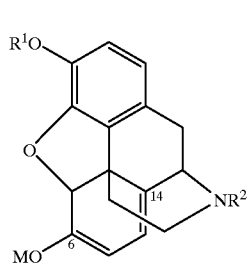

(III)

wherein R¹ and R² are as hereinbefore defined; and
M is selected from the group consisting of alkali metal and quaternary ammonium cations;
with a compound of formula R³X, wherein R³ is as hereinbefore defined and X is a leaving group; and, optionally,
the reaction of the compound of formula (I) so prepared with an acid.

2. A process according to claim 1 for preparing a compound of formula (I), wherein R¹, R² and R³ may be the same or different and are selected from $C_{1-6}$ alkyl groups.

3. A process according to claim 1 for preparing thebaine and salts thereof.

4. A process according to claim 1 for preparing thebaine bitartrate.

5. A process according to claim 1 or claim 4, wherein the compound of formula R³X is dimethyl sulphate or diethyl sulphate.

6. A process according to claim 1, which process further comprises the conversion of a salt of the compound of formula (I) so prepared to a corresponding 14-hydroxymorphinone by oxidizing said compound of formula (I) using hydrogen peroxide and then hydrogenating in the presence of a palladium catalyst to obtain said corresponding 14-hydroxymorphinone.

7. A process according to claim 6, wherein thebaine bitartrate prepared as claimed in claim 1 is converted to oxycodone.

8. A process for the preparation of a compound of formula (III):

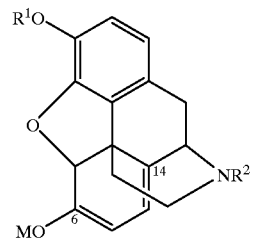

(III)

wherein R¹, R² and M are as defined in claim 1, which process comprises the reaction of a compound of formula (II):

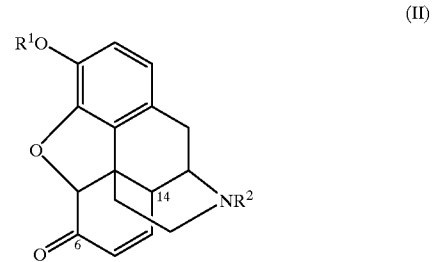

(II)

wherein R¹ and R² are as defined for formula (III), with an alkoxide base of formula MOR, wherein M is as defined for formula (III) and R is alkyl.

9. A process according to claim 8, wherein the alkoxide base is potassium tert-butoxide.

10. A process according to claim 8, wherein the reaction is carried out in a solvent.

11. A process according to claim 9, wherein the reaction is carried out in N-methylpyrrolidinone.

12. The process of claim 6 which also includes a dealkylation/deacylation step to obtain said 14-hydroxymorphinone.

* * * * *